US011413768B2

(12) United States Patent
Ruiz Morales et al.

(10) Patent No.: US 11,413,768 B2
(45) Date of Patent: *Aug. 16, 2022

(54) METHOD OF FORCE ESTIMATION FOR A MINIMALLY INVASIVE MEDICAL SYSTEM AND CORRESPONDING SYSTEM

(71) Applicant: THE EUROPEAN ATOMIC ENERGY COMMUNITY (EURATOM), REPRESENTED BY THE EUROPEAN COMMISSION, Brussels (BE)

(72) Inventors: Emilio Ruiz Morales, Taino (IT); Carlos Correcher Salvador, Valencia (ES)

(73) Assignee: THE EUROPEAN ATOMIC ENERGY COMMUNITY (EURATOM), REPRESENTED BY THE EUROPEAN COMMISSION, Brussels (BE)

(*) Notice: Subject to any disclaimer, the term of this patent is extended or adjusted under 35 U.S.C. 154(b) by 290 days.

This patent is subject to a terminal disclaimer.

(21) Appl. No.: 16/730,903

(22) Filed: Dec. 30, 2019

(65) Prior Publication Data

US 2020/0156259 A1 May 21, 2020

Related U.S. Application Data

(62) Division of application No. 15/860,616, filed on Jan. 2, 2018, now Pat. No. 10,518,419, which is a division
(Continued)

(30) Foreign Application Priority Data

Oct. 25, 2006 (EP) .................................. 06122937

(51) Int. Cl.
*B25J 13/08* (2006.01)
*A61B 34/00* (2016.01)
(Continued)

(52) U.S. Cl.
CPC ............. *B25J 13/085* (2013.01); *A61B 34/30* (2016.02); *A61B 34/35* (2016.02); *A61B 34/70* (2016.02);
(Continued)

(58) Field of Classification Search
None
See application file for complete search history.

(56) References Cited

U.S. PATENT DOCUMENTS

| 4,906,907 A | 3/1990 | Tsuchihashi et al. |
| 5,086,401 A | 2/1992 | Glassman et al. |

(Continued)

FOREIGN PATENT DOCUMENTS

| WO | 2004014244 A2 | 2/2004 |
| WO | 2005039835 A1 | 5/2005 |

OTHER PUBLICATIONS

"Improving Accuracy Through Averaging." National Instruments. National Instruments, Sep. 6, 2006 Web. http://www.ni.com/white-paper/3488/en/. May 13, 2016.
(Continued)

*Primary Examiner* — Carl H Layno
*Assistant Examiner* — Manolis Pahakis
(74) *Attorney, Agent, or Firm* — Cantor Colburn LLP

(57) ABSTRACT

A minimally invasive medical system including a robot manipulator, having an effector unit equipped with a 6-degrees-of-freedom force/torque sensor and configured to hold a minimally invasive instrument having a first end mounted
(Continued)

to the effector unit and a second end located beyond an external fulcrum that limits the instrument in motion, usually to degrees-of-freedom.

8 Claims, 3 Drawing Sheets

Related U.S. Application Data of application No. 12/447,335, filed as application No. PCT/EP2007/061494 on Oct. 25, 2007, now Pat. No. 9,855,662.

(51) Int. Cl.
  *A61B 34/30* (2016.01)
  *A61B 34/35* (2016.01)
  *A61B 90/00* (2016.01)
  *A61B 34/10* (2016.01)

(52) U.S. Cl.
  CPC .............. *A61B 34/76* (2016.02); *A61B 34/10* (2016.02); *A61B 2090/062* (2016.02); *A61B 2090/064* (2016.02)

(56) References Cited

U.S. PATENT DOCUMENTS

| | | | |
|---|---|---|---|
| 5,343,385 | A | 8/1994 | Joskowicz et al. |
| 5,382,885 | A | 1/1995 | Salcudean et al. |
| 5,397,323 | A | 3/1995 | Taylor et al. |
| 5,408,409 | A | 4/1995 | Glassman et al. |
| 5,515,478 | A | 5/1996 | Wang |
| 5,630,431 | A | 5/1997 | Taylor |
| 5,762,458 | A | 6/1998 | Wang et al. |
| 5,767,648 | A | 6/1998 | Morel et al. |
| 5,855,583 | A | 1/1999 | Wang et al. |
| 6,102,850 | A | 8/2000 | Wang et al. |
| 6,120,433 | A | 9/2000 | Mizuno et al. |
| 6,197,017 | B1 | 3/2001 | Brock et al. |
| 6,425,865 | B1 | 7/2002 | Salcudean et al. |
| 6,436,107 | B1 | 8/2002 | Wang et al. |
| 6,659,939 | B2 | 12/2003 | Moll et al. |
| 6,837,883 | B2 | 1/2005 | Moll et al. |
| 6,850,817 | B1 | 2/2005 | Green |
| 7,822,466 | B2 | 10/2010 | Stoianovici et al. |
| 8,506,555 | B2 | 8/2013 | Ruiz Morales |
| 2001/0001132 | A1 | 5/2001 | Funda et al. |
| 2002/0018046 | A1 | 2/2002 | Rosenberg |
| 2002/0169440 | A1 | 11/2002 | Jensen |
| 2003/0029463 | A1 | 2/2003 | Niemeyer |
| 2003/0040737 | A1 | 2/2003 | Merril et al. |
| 2003/0216715 | A1 | 11/2003 | Moll et al. |
| 2004/0140787 | A1 | 7/2004 | Okamoto et al. |
| 2005/0021050 | A1 | 1/2005 | Cooper |
| 2005/0113971 | A1 | 5/2005 | Zhang et al. |
| 2005/0119783 | A1 | 6/2005 | Brisson et al. |
| 2006/0161045 | A1 | 7/2006 | Merril et al. |
| 2006/0161137 | A1 | 7/2006 | Orban, III et al. |
| 2006/0264915 | A1 | 11/2006 | Jensen |
| 2007/0016067 | A1 | 1/2007 | Webster, III et al. |
| 2007/0018958 | A1 | 1/2007 | Tavakoli et al. |
| 2007/0156157 | A1 | 7/2007 | Nahum et al. |
| 2009/0024142 | A1 | 1/2009 | Ruiz Morales |
| 2010/0204713 | A1 | 8/2010 | Ruiz Morales |
| 2011/0125165 | A1 | 5/2011 | Simaan et al. |
| 2013/0030571 | A1 | 1/2013 | Ruiz Morales et al. |
| 2018/0194013 | A1 | 7/2018 | Morales |

OTHER PUBLICATIONS

Alexandre Krupa et al. "Achieving High Precision Laparoscopic Manipulation Through Adapttive Force Control", International Conference on Robotics & Automation, Proceedings of IEEE, May 2002, pp. 1864-1869, Washington, D.C.

B. Kuebler et al., "Development of Actuated and Sensor Integrated Forceps for Minimally Invasive Robotic Surgery", International Journal Medical Robotics and Computer Assisted Surgery, Sep. 2005, vol. 1 (3); pp. 96-107, www.roboticpublications.com.

Beke et al, Whisker Sensor Design for Three Dimensional Position Measurement in Robotic Assisted Beating Heart Surgery, 2007 IEEE International Conference on Robotics and Automation Roma, Italy.

Berkelman et al., A Miniature Instrument Tip Force Sensor for Robot/Human Cooperative Microsurgical Manipulation With Enhanced Force Feedback, MICCAI 2000, LNCS 1935, pp. 897-906, 2000.

Christopher W. Kennedy et al. "Force Feedback Using Vision", International Conference on Advanced Robotics, 2003, 7 pgs., Coimbra, Portugal.

Derek B. Kingston et al. "Real-Time Attitude and Position Estimation for Small UAVs Using Low-Cost Sensors", American Institute of Aeronautics and Astronautics, pp. 1-9, 2004.

Jason Matthew Henry, Theory and Implementation of the Naturally Transitioning Rate-to-Force Controller Including Force Reflection Using Kinematically Dissimilar Masterislave Devices, Thesis, Ohio University, 1999.

Louis Drolet et al. "Adaptable Sensor Fusion Using Multiple Kalman Filters", International Conference on Intelligent Robots and Systems, 2000, 6 pgs.

Peter J. Berkelman et al. "A Miniature Microsurgical Instrument Tip Force Sensor for Enhanced Force Feedback During Robot-Assisted Manipulation", IEEE Transactions on Robotics and Automation, Oct. 2003, pp. 917-922, vol. 19, No. 5.

Rosen et al, Markov Modeling Ofminimally Invasive Surgery Based on Tool/Tissue Interaction and Force/Torque Signatures for Evaluating Surgical Skills, IEEE Transactions on Biomedical Engineering, vol. 48, No. 5, May 2001.

Starkle SJ, Study Report-Neuro-Endopcopic Manipulator, Apr. 14, 1998.

Tobias Ortmaier et al. "A New Robot for Force Control in Minimally Invasive Surgery", IEEE/RSJ International Conference on Intelligent Robots and Systems, 2004, 8 pgs, Japan.

Williams, RL, Cartesian Control of Force-Reflecting Hand Controllers, Proceedings of the Fifth National Conference on Applied Mechanisms and Robotics, Cincinnati OH, 1997.

Zemiti et al., "A Force Controlled Laparoscopic Surgical Robot without Distal Force Sensing", Experimental Robotics IX, Star 21 , 2006, pp. 1-12.

Zemiti et al., "A New Robot for Force Control in Minimally Invasive Surgery", Proceedings of 2004 IEEE/RSJ International Conference on Intelligent Robots and Systems, Sep. 28-Oct. 2, 2004, pp. 1-6.

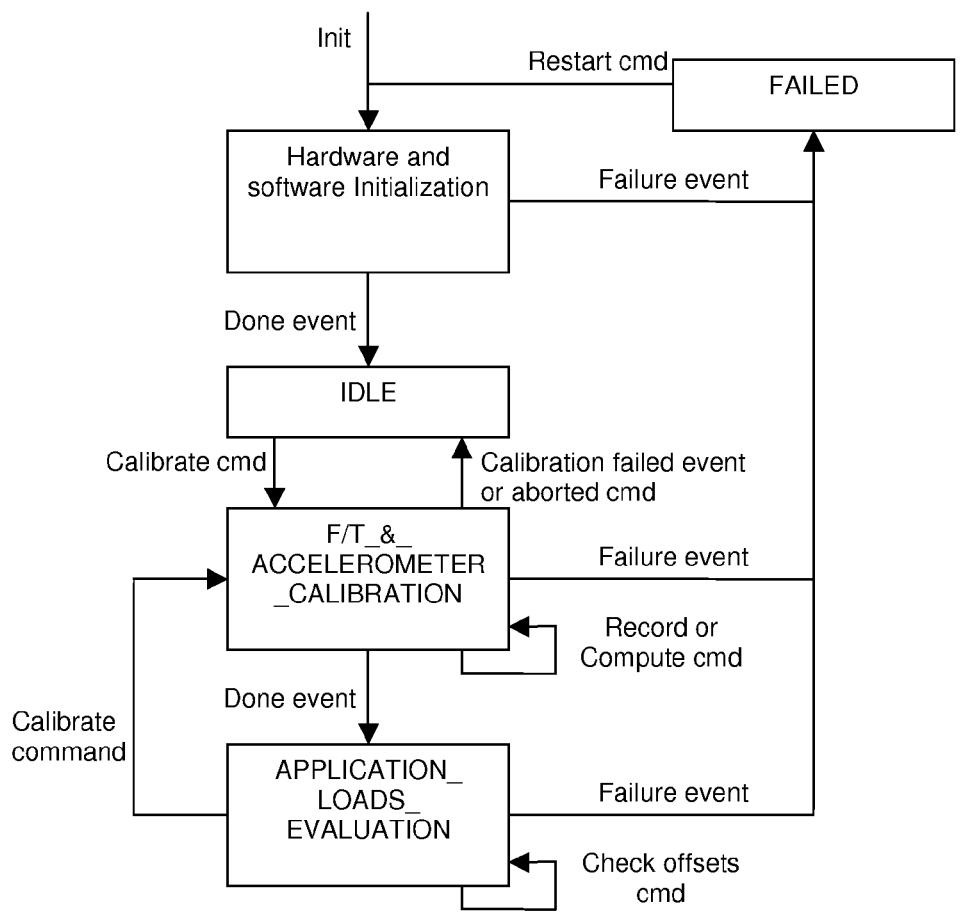
FIG.6
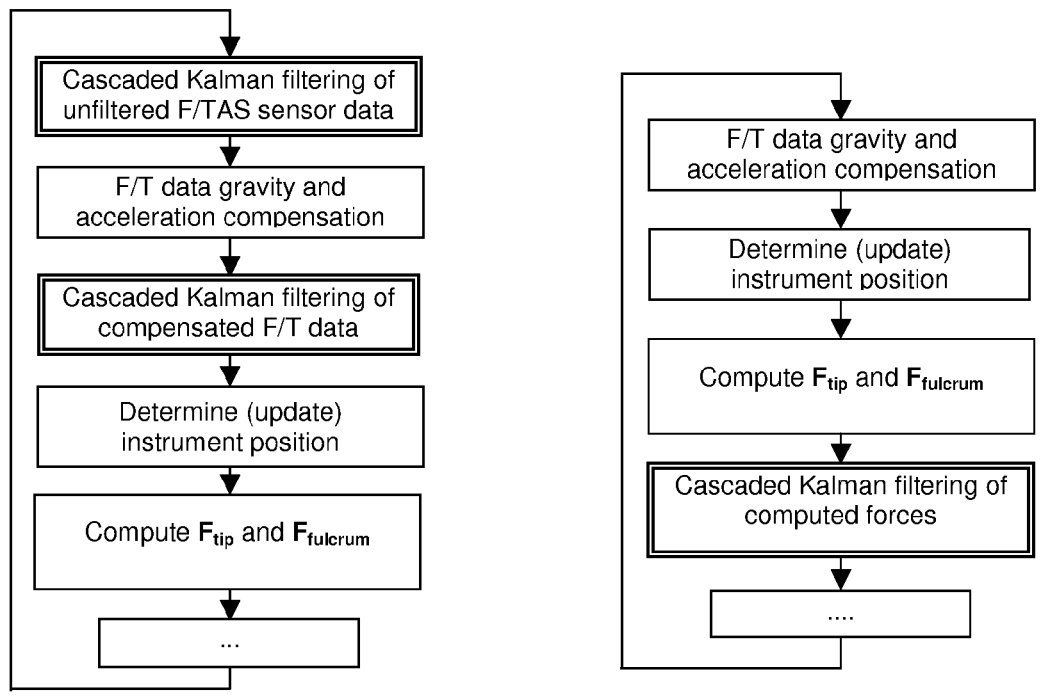
FIG.7
FIG.8

METHOD OF FORCE ESTIMATION FOR A MINIMALLY INVASIVE MEDICAL SYSTEM AND CORRESPONDING SYSTEM

CROSS REFERENCE TO RELATED APPLICATION

This application is a divisional of U.S. patent application Ser. No. 15/860,616 filed on Jan. 2, 2018, now U.S. Pat. No. 10,518,419 which granted on Dec. 31, 2019 and which was a divisional of U.S. patent application Ser. No. 12/447,335 filed on Apr. 27, 2009, which granted as U.S. Pat. No. 9,855,662 on Jan. 2, 2018 and which was filed under 35 USC 371 as the U.S. national phase of International Patent Application Number PCT/EP2007/061494 filed on Oct. 25, 2007, which claimed priority to European Patent Application Number 06122937.3 filed on Oct. 25, 2006, all of which said applications are incorporated herein by reference in their entirety.

TECHNICAL FIELD

The present invention generally relates to the field of minimally invasive medical procedures, including surgery and diagnostic procedures. More particularly, the invention concerns a method and a system for force estimation that are capable of determining forces exerted onto a patient, especially by the tip of a minimally invasive instrument, but also at the level of the access port for the instrument into the patient body.

INTRODUCTION

It is well known that minimally invasive interventions have the benefit of reducing the amount of extraneous tissue that is damaged during diagnostic or surgical procedures. This results in shorter patient recovery time, less discomfort, less deleterious side effects and lower costs of the hospital stay. Nowadays, in general surgery, urology, gynecology and cardiology specialties, there is an increase of the amount of interventions carried out by minimally invasive techniques, such as laparoscopic techniques.

Manual minimally invasive techniques in general, and laparoscopy in particular, put stringent requirements on the surgeon carrying out the operation. The surgeon operates in an uncomfortable and tiring posture, with a limited field of view, reduced dexterity and poor tactile perception. To these problems adds the fact that surgeons often have to carry out several consecutive interventions per day, each intervention lasting e.g. from 30 minutes to several hours. In spite of the inherent difficulties, the trend towards minimally invasive procedures is expected to increase further in the coming years due to an increasing average age of the population and pressure of costs in the medical field.

In laparoscopy for example, surgeons are obviously required to be as precise in his moves as in laparotomy. Manipulating long-shaft instruments with motion dexterity reduced to four degrees of freedom about a fulcrum (pivot point) at the instrument access port (also called trocar), i.e. at the incision in the patient body, is not alleviating their task. Complications arise inter-alia by the fact that the required posture is often tiresome and reduces the already limited perception of interacting forces between instrument and tissues. As a result, motorial capabilities of a surgeon normally decay after 20-30 minutes, such that among others trembling, loss of accuracy and loss of tactile sensitivity occur with the resulting risks for the patient. Therefore, new computer and/or robot assisted technologies, such as Minimally Invasive Robotic Surgery (MIRS), are emerging. These technologies aim at improving efficiency, quality and safety of intervention.

BACKGROUND ART

In view of the above, MIRS has known significant development during the last decade. Two representative commercial robotic systems are the system known by the trademark 'DA VINCI' developed by Intuitive Surgical Inc., Sunnyvale, Calif. and the system known by the trademark 'ZEUS' originally developed by Computer Motion Inc., Goleta, Calif. The system known by the name 'DA VINCI' is described among others by Moll et al. in U.S. Pat. Nos. 6,659,939; 6,837,883 and other patent documents of the same assignee. The system known by the name 'ZEUS' is described among others by Wang et al. in U.S. Pat. Nos. 6,102,850; 5,855,583; 5,762,458; 5,515,478 and other patent documents assigned to Computer Motion Inc., Goleta, Calif.

These teleoperated robotic systems permit to control surgical interventions either directly from the operation theatre or from a remote site, generally using 2-dimensional or 3-dimensional visual feedback only. In either case, the tiring posture of the surgeon is eliminated. Furthermore, these systems tend to give the surgeon the feeling to work in open conditions, e.g. as in laparotomy, and eliminate the aforementioned tiresome posture.

Currently available teleoperated MIS systems typically do not offer true tactile force feedback (referred to as force feedback below) on the console by means of which the surgeon commands the robot(s). Hence the surgeon lacks a true haptic feeling of the forces exerted onto organs and tissues. With such systems, the surgeon has to rely on visual feedback and on his experience to limit interaction of instruments with the intra-patient environment. In this respect, research work has been done concerning a computer-assisted sensorless force feedback system based on the concept that a computer could reproduce what a surgeon skilled in manual MIS procedures is capable of. In other words, a computer could estimate forces from deformations observed by vision. An example of such attempts is found in: "Force feedback using vision"; Kennedy, C. and Desai, J. P.; International Conference on Advanced Robotics; Coimbra, Portugal, 2003. Such systems have however not yet reach a commercially viable state.

As will be appreciated, accurate force feedback is considered a crucial feature to ensure operation safety and to improve the quality of procedures carried out with machine assisted minimally invasive systems. Therefore, force feedback is believed to be of paramount importance for teleoperated interventions.

At the instrument tip level, force sensing allows for example palpation of organs and tissues, which is highly desirable in diagnostic procedures and for identifying critical areas e.g. with arteries. Other possible enhancements consist in the limitation of stretching tension on sutures and the limitation of exerted forces on tissues according to the type and specific phase of the intervention. In practice, contact forces can be kept below a given threshold by increasing motion scales, stopping the manipulator motion, or increasing force feedback on the master device. Furthermore, force sensing would permit to work intuitively with an instrument that is not in the field of view of the endoscope camera, e.g. when the surgeon assistant holds an organ away from the operation field.

At the access port level, force sensing would be beneficial in order to monitor and consequently reduce forces applied by the instrument at the incision for the access port. These forces are the main cause of incision wear that can lead to loss of abdominal pressure, release of the trocar, and increased intervention time due to the need to recover the situation. These detrimental forces are mainly caused by the inaccurate location of the instrument fulcrum (pivot point), as determined by the system and modified due to variations of intra-abdominal pressure, with respect to the patient incision but also by motion drifts of the (robot) manipulator due to its positioning inaccuracy. In manual interventions, these wearing forces are less pronounced because of the human capability to intuitively adjust hand motion with respect to the optimal pivot point in the incision.

To overcome the trocar-release problem, the aforementioned DA VINCI system for example, uses a trocar attached to the manipulator wrist at the extremity of the instrument insertion/extraction slide. This solution does not reduce the risk the incision wear and does not improve the loss of abdominal pressure.

In order to overcome the latter problem at the trocar level, a force-feedback adaptive controller, which is capable of automatically adjusting the fulcrum point of a robot manipulator on a plane tangent to the abdomen of the patient, has been developed and described in the paper "Achieving High Precision Laparoscopic Manipulation Through Adaptive Force Control"; Krupa, A. Morel, G. De Mathellin M.; Proceedings of the 2002 IEEE Intern. Conference on Robotics and Automation; Washington D.C., May 2002. In this approach, a sensor on the end-effector of a robot in combination with a force controller is used to explicitly regulate the lateral forces exerted onto the trocar, which together with the abdominal wall defines the fulcrum, towards zero. This method and system are not capable of determining the forces at the tip of the instrument inserted through the trocar. Instead, the interaction force at the instrument tip is assumed to be negligible. Therefore, this method can be satisfactorily used only with an endoscope manipulator that does not have any other contact point with the patient.

A different approach is described in the paper: "Development of actuated and sensor integrated forceps for minimally invasive robotic surgery"; B. Kübler, U. Seibold and G. Hirzinger; Jahrestagung der Deutschen Gesellschaft für Computer- und Roboterassistierte Chirurgie (CURAC), October 2004. This paper describes a miniaturized 6 DOF force/torque sensor to be installed at the tip of a minimally invasive instrument. This sensor enables accurate sensing of the forces exerted by the instrument tip and corresponding force feedback. This concept has several drawbacks however, among which manufacturing and installation cost, the lack of robustness in autoclave sterilization, and EMI shielding issues when combined with powered instruments. As will be understood, a dedicated sensor has to be provided on every instrument when using this approach. A similar approach has been described in the paper: "A miniature microsurgical instrument tip force sensor for enhanced force feedback during robot-assisted manipulation"; Berkelman, P. J., Whitcomb, L. L., Taylor, R. H., and Jensen, P.; IEEE Transactions on Robotics and Automation, October 2003.

A different approach, which does not require a tip mounted sensor on every instrument has been described in the paper "A New Robot for Force Control in Minimally Invasive Surgery"; Zemiti N., Ortmaier T. et Morel G.; IEEE/RSJ International Conference on Intelligent Robots and Systems, Japan, 2004. This paper describes a robot and force sensor arrangement that can measure the distal organ-instrument interaction with a sensor placed on the trocar. Even though, in this approach, the sensor is not mounted on the instrument itself and is therefore subject to lower miniaturization and sterilization constraints, this solution still requires modified trocars with sensor equipment capable of resisting sterilization. A further approach designed for MIS, as disclosed in patent application WO 2005/039835, uses a master/slave architecture with two PHANTOM® haptic devices developed by SensAble Technologies, Woburn, Mass. This system comprises a first PHANTOM device integrated into a slave subsystem and serving as manipulator for an instrument in combination with an effector subassembly that is configured for holding and mounting an off-the shelf instrument tip of a minimally invasive instrument such as graspers, dissectors, scissors, etc. to the first PHANTOM device. In operation, the minimally invasive instrument has a first end mounted to the effector subassembly and a second end located beyond an external fulcrum that limits the instrument in motion. In order to provide measurement of the force vector ($f_x$, $f_y$, $f_z$) and the moment ($\tau_z$) at the end of the instrument tip, a custom made arrangement of various strain gauges is provided. Furthermore, the system comprises one or more personal computers with application programs for controlling and serving the first PHANTOM device of the slave subsystem and a second PHAMTOM device of the master subsystem.

Technical Problem

It is an object of the present invention to provide a method and system that permit to estimate the force exerted onto, respectively by, the instrument tip in cost-effective and efficient manner while avoiding the need for trocar and/or instrument tip mounted sensors.

GENERAL DESCRIPTION OF THE INVENTION

To achieve this object, the invention proposes a method of force estimation and a minimally invasive medical system, in particular a laparoscopic system, adapted to perform this method. The system comprises a manipulator, e.g. a robot manipulator, that has an effector unit equipped with a six degrees-of-freedom (6-DOF or 6-axes) force/torque sensor. The effector unit is configured for holding a minimally invasive instrument mounted thereto. In normal use, a first end of the instrument is mounted to the effector unit and the opposite, second end of the instrument is located beyond an external fulcrum (pivot point kinematic constraint) that limits the instrument in motion. In general, the fulcrum is located within an access port (e.g. the trocar) installed at an incision in the body of a patient, e.g. in the abdominal wall. According to the invention, the method comprises the following steps:

determining a position of the instrument relative to the fulcrum (which in the present context especially means continuously updating the insertion depth of the instrument or the distance between the (reference frame of the) sensor and the fulcrum);

measuring by means of the 6 DOE force/torque sensor a force and a torque exerted onto the effector unit by the first end of the instrument; and calculating by means of the principle of superposition an estimate of a force exerted onto the second end of the instrument based on the determined position, the measured force and the measured torque.

The system comprises a programmable computing device, such as a standard computer, a Digital Signal Processor (DSP) or a Field Programmable Gate Array (FPGA), programmed to determine the instrument position, to process the measurements made by the 6 DOF force/torque sensor and to calculate the force estimate as set out above.

The method and system enable estimation (which in the present context especially means determination of value(s) that may be affected by a small inaccuracy) of the force exerted onto a tissue or organ of patient by the second end of the instrument, i.e. the instrument tip, which is invasively introduced into the patient through an access port such as a trocar. Indeed, the latter force is equivalent to the actio of the opposite force estimated by the method (reactio). As will be appreciated, this method further enables a system design, which requires only a single sensor unit that includes the 6-DOF force/torque sensor and mounted on the manipulator i.e. outside the patient. Conveniently, the sensor unit is mounted in force transmission between the connection interface for the instrument on the effector unit and the extreme link/member of the manipulator that supports the effector unit. In other words, the 6-DOF force/torque sensor is arranged for sensing forces and torques exerted onto the effector unit by the first end (=mounted end) of the instrument.

Hence, the present invention overcomes the well established general opinion that sensory equipment must be provided at the level of the instrument tip and/or the trocar in order to achieve accurate force measurements of forces exerted at the instrument tip. It thus eliminates expensive dedicated sensory equipment to be provided on the tip of every instrument as well as and on the trocar, that would be subject to stringent miniaturization and sterilization constraints. With the presented method and system, the latter constraints are overcome, while a surprisingly accurate estimation of the contact force at the instrument tip can be achieved.

It will be understood that the presented method/system can be used in connection with a manually operated manipulator (instrument positioning stand) or, more commonly, with a robot manipulator. The method/system enables among others a facilitated implementation of force-feed back and automated safety features in tele-operated medical systems, such as minimally invasive robotic surgery and diagnostic systems. For example, tactile sensing on a force-reflecting (haptic) master arm of an operating console for the surgeon as well as an automated procedure for limiting the maximum force exerted by the instrument tip onto a patient's organ(s) and tissue(s) can be implemented using information gained with the present method/system.

In a preferred embodiment, the method comprises determining an initial reference position of the instrument relative to the fulcrum. In this embodiment, determining the position of the instrument relative to the fulcrum is based on the determined initial reference position and on continuous updating using manipulator motion information. This effective procedure takes advantage of known information such as coordinate information by direct kinematics of a robot manipulator.

Preferably, the method further comprises the step of calculating by means of the principle of superposition an estimate of a force exerted at the fulcrum by the instrument, e.g. onto the trocar, based on the determined position, the measured force and the measured torque. Knowledge of the force exerted onto the tissue of a patient at the incision level, of which the force exerted at the fulcrum is the reactio (with opposite sign), allows among others automated (re)adjustment of the fulcrum coordinates, which are e.g. used by a robot controller for reducing stresses and loads exerted onto the tissue of the patient at the incision level. Furthermore, an automated procedure for limiting the maximum force exerted at the access port level can be implemented.

Preferably, the effector unit is further equipped with a 6-DOF accelerometer. In this case, the method preferably further comprises the steps:
 measuring by means of the 6-DOF accelerometer a gravity load and dynamic loads exerted onto the 6-DOF force/torque sensor; and
 compensating the gravity and/or dynamic loads in the measured force and the measured torque.

Such compensation allows to improve the accuracy of the desired force estimate(s) at the instrument tip and/or at the fulcrum level.

Advantageously, the method further comprises a calibration procedure including the additional steps:
 passing the effector unit through a set of poses distributed over a workspace, in particular the orientation workspace, of the manipulator;
 recording for each pose a measured force and a measured torque; and
 determining force and torque measurement offsets based on the recorded force and torque measurements.

In a further preferred embodiment, in case the 6-DOF accelerometer is provided, the calibration procedure further comprises the steps:
 recording for each pose a measured linear acceleration and a measured angular acceleration; and
 determining linear and angular acceleration measurement offsets based on the recorded linear and angular acceleration measurements.

The calibration procedure allows determining (electrical) offsets in the measurement signals provided by the sensors and further useful system parameters, knowledge of which enables further improvements in the accuracy of the desired force estimate(s).

For reducing measurement signal noise, the method advantageously comprises applying a linear Kalman filter (according to the basic as opposed to e.g. the non-linear extended Kalman formulation) to force and torque data measured by the 6 DOF force/torque sensor prior to calculating the estimated force or applying a linear Kalman filter to the calculated force estimate, i.e. after the estimated force(s) have been calculated. Among the many available filter types, the basic linear Kalman filter has been found to be a simple, reliable and fast filter for removing signal noise in the measured components.

In case the accelerometer is provided, the method may preferably comprise the steps:
 applying a primary linear Kalman filter to force and torque data measured by the 6 DOF force/torque sensor and to linear and angular acceleration data measured by the 6 DOF accelerometer;
 compensating disturbances due to gravity and dynamic loads after application of the primary linear Kalman filter;
 applying a secondary linear Kalman filter to the compensated force and torque data.

Every Kalman filter for each force/torque and acceleration component should cause the same filter inherent response-delay. In case there is excessive noise in the force component estimates after compensation (due to acceleration signals being noisier than the force/torque measurements), a secondary filter after disturbance compensation is preferred. The primary filter reduces noise-induced falsification during compensation whereas the secondary filter allows smoothing the compensation results.

Preferably, the Kalman filter, respectively the primary and/or secondary Kalman filter, is cascaded and has a first linear Kalman filter stage with a process noise covariance parameter set to a higher value, preferably in the range between 0.1 and 1, and a second linear Kalman filter stage with a process noise covariance parameter set to a lower value, preferably in the range between 0.001 and 0.1. At a given measurement noise covariance, the cascaded filter configuration enables lower total response-delays when compared to a single stage filter for a given noise reduction capacity.

As will be appreciated, the system is adapted for use with a sensorless minimally invasive instrument. It further beneficially comprises a sensorless trocar, preferably with a magnetic-based air-valve and especially without plastic cap. Furthermore the system advantageously comprises a trocar without gas tap which is preferably made to the major extent of plastic material so as to save weight.

The system may comprise a software program stored by the programmable computing device, which includes program code for performing all the steps of any one of the above embodiments of the method when the software program is run on the programmable computing device. The invention also concerns a software program product comprising program code stored on a machine-readable storage medium which, when running on programmable computing device or loaded onto a programmable computing device, causes the programmable computing device to perform all the steps of any one of the above embodiments of the method.

While the present patent application as filed in principle concerns the invention as defined in the claims attached hereto, the person skilled in the art will readily understand that the present patent application contains support for the definition of other inventions, which could e.g. be claimed as subject matter of amended claims in the present application or as subject matter of claims in divisional and/or continuation applications. Such subject matter could be defined by any feature or combination of features disclosed herein.

BRIEF DESCRIPTION OF THE DRAWINGS

Further details and advantages of the present invention will be apparent from the following detailed description, which is not intended to be limiting, with reference to the attached drawings, wherein:

FIG. 6 is a state transition diagram of the main task (FSS task) of the architecture in FIG. 5;

FIG. 7 is a flow chart of a sequence of program steps to be carried out cyclically during the APPLICATION_LOADS_EVALUATION state of FIG. 6;

FIG. 8 is a flow chart of an alternative sequence of program steps to be carried out cyclically during the APPLICATION_LOADS_EVALUATION state of FIG. 6.

DETAILED DESCRIPTION OF PREFERRED EMBODIMENTS

System Components and Mechanical Configuration

Figure 1:
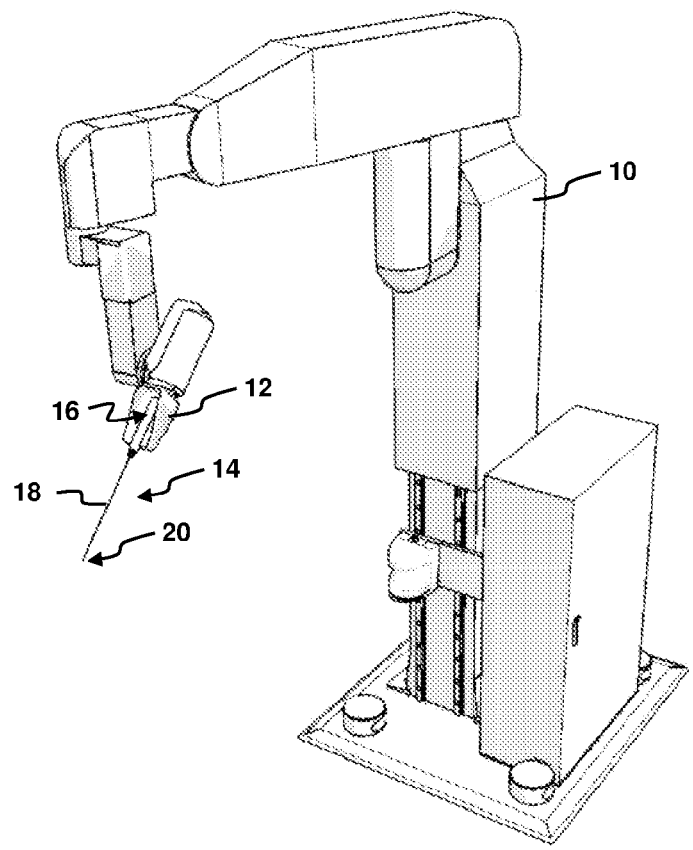
FIG. 1 is a perspective view of a robot manipulator for a minimally invasive medical system according to a preferred embodiment of the invention.

FIG. 1 shows the main mechanical components of the minimally invasive medical system according to the invention. The system comprises a robot manipulator, generally identified by reference numeral 10. An effector unit 12 is connected to a flange of the manipulator 10. A minimally invasive instrument 14, is mounted with a first end 16 to the effector unit as shown in FIG. 1. The instrument 14 comprises an elongated shaft 18 with a tip 20 forming the second end of the instrument 14. At its tip 20, the instrument 14 normally comprises a specific tool e.g. grasper, scissor, hook, coagulator, etc. The robot manipulator 10 itself provides 6 degrees of freedom (DOF) by means of a PRP-RRR joint arrangement for positioning and orienting the effector unit 12, the effector unit 12 being mounted to the foremost rotational (R) joint for rotating the minimally invasive instrument 14 about the $6^{th}$ DOF of the manipulator 10 which coincides with the longitudinal shaft axis of the instrument 14. As will be appreciated, the robot manipulator 10 provides a 6 axis positioning and orienting device capable of replicating the motion of a surgeon's hand by moving the effector unit 12.

Figure 2:
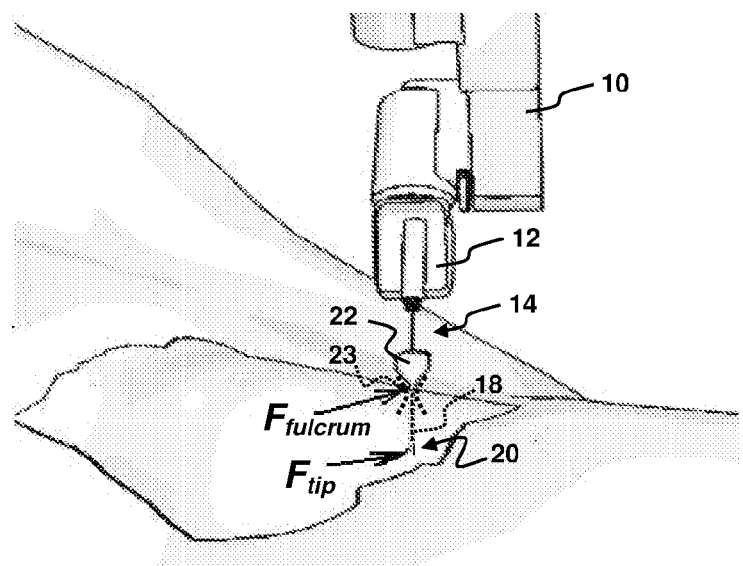
FIG. 2 is a partial perspective view of a minimally invasive instrument, the tip of which inserted into a patient and the opposite end of which is mounted to an effector unit of the robot manipulator of FIG. 1, for illustrating a fulcrum force and a tip force.

FIG. 2 shows the instrument 14, mounted to the effector unit 12 of the robot manipulator 10, in operational position for performing a minimally invasive medical procedure. As indicated by a dashed line in FIG. 2, the shaft 18 of the instrument 12 is partially inserted into a patient's body, e.g. into the abdomen of a patient. The instrument slideably penetrates through an access port, referred to as trocar 22 hereinafter. The first end of the instrument 14, i.e. the tip 20 is located beyond a fulcrum, indicated by cross-shaped broken lines at 23, (also called pivot point) defined by the trocar 22 which is inserted into an incision in the patient's abdominal wall and fixed thereto.

In normal use, the fulcrum is a kinematic constraint that allows rotation around three axes (e.g. two orthogonal pivot directions and one rotation about the instrument axis, i.e. the Z axis in the SRF defined below) but translation of the instrument 14 only along the penetration axis (e.g. of the trocar 22-Z in the SRF defined below). The fulcrum is defined by the access port, e.g. by the trocar 22, and/or the tissue of the patient in which the incision is provided, e.g. the patient's abdominal wall.

FIG. 2 schematically indicates two forces $\overline{F_{Fulcrum}}$ and $\overline{F_{Tip}}$. $\overline{F_{Tip}}$ is a force exerted onto the instrument tip 20 and therefore represents the reactio corresponding to the (opposite) force (actio) that the instrument tip 20 exerts on an internal organ or tissue of the patient. $\overline{F_{Fulcrum}}$ is a force exerted onto the trocar 22 and therefore represents the reactio corresponding to the (opposite) force (actio) that the trocar 22, which is subject to loads exerted thereon by the instrument shaft 18, exerts onto the patient's abdominal wall. The proposed method for determining both, $\overline{F_{Tip}}$ and $\overline{F_{Fulcrum}}$ will be described hereinafter.

Although not shown in the figures, the system further comprises a manipulator controller, i.e. hardware, e.g. in the form of a main computer, programmed with software for operating one or more robot manipulators 10. Furthermore, a command console for tele-operation with a force reflection master arm, i.e. a haptic interface for force-feedback, is used by an operator, e.g. a surgeon, to command the robot manipulator 10 via the manipulator controller. As will be understood, the estimate of $\overline{F_{Tip}}$ will be fed to the haptic interface for providing force-feedback and to the motion controller for safety functions. The motion controller also uses the estimate of $\overline{F_{Fulcrum}}$ for safety functions and for readjusting the assumed coordinates of the fulcrum 23.

Figure 3:
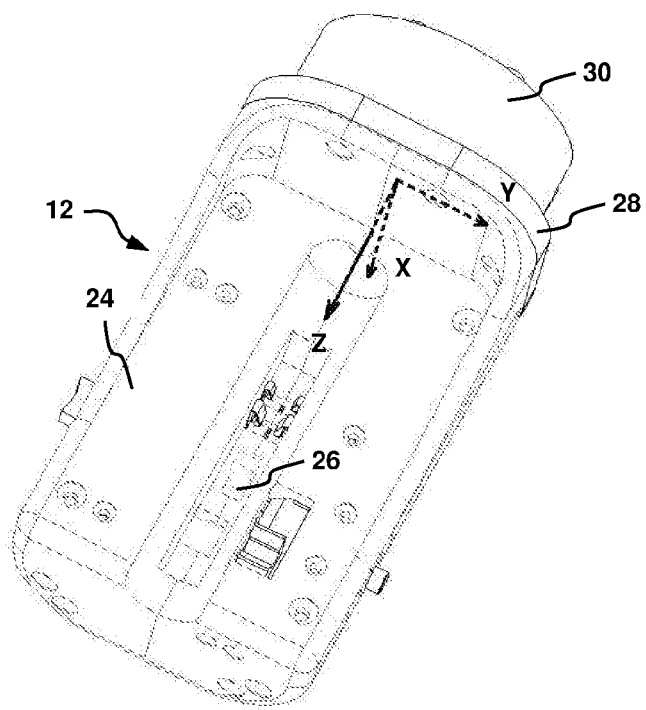
FIG. 3 is an enlarged perspective view of the effector unit shown in FIG. 2, illustrating a reference coordinate frame of a force/torque and acceleration sensor provided on the effector unit.

FIG. 3 shows an enlarged view of the effector unit 12 which is arranged to support the first end 16 of the instrument 14 (not shown in FIG. 3) in mechanically rigid manner and further provided with actuating means for actuating certain types of instruments and signal and power connection means for electrically connecting the instrument 14 to the system. The effector unit 12 comprises a rigid main body 24 including the actuating and connection means as well as a socket 26 to which an adapter at the first end 16 of the instrument 14 (not shown) can be rigidly connected. At its rear end, the main body 24 comprises a connection flange 28 by means of which it is rigidly fixed to the sensing plate of a 12-DOF (i.e. 12 axis) force/torque and acceleration sensor 30, referred to as F/TAS 30 hereinafter. The F/TAS 30 may be configured as single sensor unit comprising a 6-DOF force/torque sensor, referred to as F/T sensor hereinafter, for sensing forces and torques on three orthogonal axes, and a built-in 6-DOF accelerometer, for sensing linear and angular acceleration about the three orthogonal axes. Alternatively, a 6-DOF force/torque sensor with an appropriately associated separate 6-DOF accelerometer can also be used. The F/TAS 30 in turn is rigidly fixed to the robot manipulator 10, as seen in FIG. 1. Instead of the described F/TAS 30, a sensor unit comprising only a 6-DOF F/T sensor (i.e. no accelerometer) can be used. In the latter case, acceleration components can be determined using the second derivative of position coordinates of the end-effector (e.g. effector unit 12) obtained e.g. by direct kinematic computation using articulation positions. Compensation of dynamic loads as described hereinafter can thus be achieved without accelerometer. It may be noted that the effect of gravity can also be compensated without accelerometer since the gravity vector is known and the orientation and center of gravity of the payload attached to the F/T sensor can be determined.

FIG. 3 further shows the Cartesian reference coordinate frame of the F/TAS 30, with the three orthogonal axes X, Y and Z, hereinafter referred to as SRF (sensor reference frame). As will be understood, the 6 DOF of the F/T sensor in the F/TAS 30 correspond to 3 DOF for X, Y and Z force components respectively and 3DOF for moments (torque values) about the X, Y and Z axes respectively, in the SRF. In case a separate 6-DOF accelerometer is attached to a 6-DOF F/T sensor for providing the F/TAS 30, the reference coordinate frame of the accelerometer is preferably coincident with the reference coordinate frame of the F/T sensor. Otherwise, an additional transformation between these two Cartesian frames shall be added in the calculations described hereinafter. In the embodiment shown in FIGS. 1-3, the 12 axis F/TAS 30 comprises a built in 6-DOF accelerometer. The 6 DOF of the accelerometer correspond to linear acceleration components along and angular acceleration components about the X, Y and Z axes respectively, in the SRF shown in FIG. 3.

As will be understood, the effector unit 12 is rigidly fixed to the sensing plate of F/TAS 30 and preferably configured such that the longitudinal (shaft) axis of a mounted instrument 14 (cf. FIG. 2) is collinear with one axis of the SRF of the F/TAS 30, preferably the Z axis as seen in FIG. 3. Otherwise, an additional transformation shall be added in the calculations described hereinafter.

Main Disturbance Sources and Analysis Thereof

The present section gives an overview of main disturbance sources that affect the desired estimation of the force at the instrument tip 20, with the system presented in FIGS. 1-3.

Besides the intrinsic F/T sensor disturbances such as sensor offsets, electrical noise and temperature drifts, with the present system there are, as opposed to other known force sensing systems (e.g. using a F/T sensor mounted on the instrument tip), a number of additional disturbing and masking factors to be taken into account. As regards measured force and moment information, these are mainly:

static and dynamic loads exerted onto the F/T sensor: static loads due to gravity (weight of the mass attached to the manipulator mounted F/TAS 30), dynamic loads due to the velocity and acceleration of the payload attached to the F/T sensor;

disturbance sources related to the minimally invasive medical procedure: trocar friction forces in the penetration and extraction direction due to the trocar gas tap and the air valve, resistance to pivot due to the trocar gas tap, the modification of the fulcrum 23 (pivot point) due to the variations of abdominal insufflation pressure, inaccurate definition of the fulcrum 23, modification of the fulcrum 23 due to inaccuracy of the manipulator 10 while moving.

Disturbing forces produced by the trocar friction: The trocar 22 produces friction along the penetration/extraction axis. The friction magnitude depends on the type of air-valve used in the trocar 22 (e.g. magnetic, spring-based or plastic membrane type), on the plastic cap wear, on the material of the instrument shaft 18 and on its internal lubrication by irrigation water and viscous intra-abdominal fluids. According to laboratory trials, friction caused by magnetic and spring-based air-valves can be approximated by a Coulomb friction in a range of 0.5N-0.9N and does not depend on lubrication conditions. In practice, the spring-based air-valve friction depends slightly on its wear, and is higher than magnetic air-valves friction by approximately 0.3 N. The plastic membrane air-valve and the plastic cap produce a Coulomb friction but also an impulse-like reaction force when inverting the instrument direction. This reaction component is opposed to the motion direction and is mainly caused by the plastic collar reversal. The membrane and cap friction depends on the membrane cut geometry and on the type of material, but is attenuated by lubrication of the trocar 22 which increases along with the intervention time through instruments moves. In dry laboratory trials using standard trocars, plastic caps produce a Coulomb friction in the range of 1N-1.5N, and plastic membrane air-valves give a Coulomb friction in the range of 6N-10N. In addition, the friction magnitude is found to be asymmetric with respect to the penetration and extraction directions. For plastic membrane valves, smaller friction amplitude was observed in the penetration direction. Therefore, in order to reduce the penetration and extraction friction at the trocar 22 as much as possible, magnetic-based air-valves, possibly without plastic cap, are preferred Disturbing forces produced by trocar gas tap: Some types of trocars have a tap for insufflating gas. The tap and the connected gas tube can act as obstacles when pivoting the trocar 22, resulting in a disturbing resistance force opposed to the pivot direction. The magnitude of this force depends on the stiffness of the abdominal wall and is generally between 2N and 5 N according to laboratory trials. Hence, use of trocars with gas tap should be avoided with the presented system.

Disturbing force produced by the trocar weight: Multiple-use trocars are usually lightweight, from 30 g to 80 g, and made of stainless steel possibly with some parts made of plastic. Trocars with a gas tap have a cylindrical reservoir and are heavier, ranging from 100 g to 180 g. The trocar weight can be perceived as a disturbing force along the transversal X and Y axes in the SRF, depending on the orientation of the trocar 22 with respect to the gravity vector. Therefore, lightweight trocars made with plastic parts are preferred with the proposed system.

Disturbing forces produced by low intra-abdominal pressure: In nominal laparoscopy conditions, the abdominal wall is a relatively stiff surface to which the trocar 22 is attached. In case of low intra-abdominal pressure, the trocar friction magnitude may become higher than the resistance offered by the abdominal wall. In this case, instrument penetration or extraction can move the trocar 22 inwards or outwards up to the point where the abdominal wall tension overcomes the trocar friction. Negative side-effects are firstly, that the location of the fulcrum 23 is altered with respect to the abdominal wall, whereby disturbing loads during pivoting increase due to the interaction of the instrument with the abdominal wall, and secondly, a spring-like load (with a maximum value equal to the trocar friction) is applied in the direction opposite to the instrument motion. In order to avoid these disturbing forces, the intra-abdominal pressure is preferably continuously monitored and maintained. In case of depressurization, a warning is issued in order to take appropriate actions, such as adjusting fulcrum position in the manipulator controller.

Disturbing forces from inaccuracies in the determination of the fulcrum location: In manual laparoscopic surgery, the surgeon naturally moves the instrument with respect to the minor tilting resistance point, which is the ideal fulcrum 23 (pivot point), located at about the height of the stiffest layer of the abdominal wall, inside the trocar 22. When using a robot manipulator 10 for handling the instrument 14, without any specifically designed mechanical compliance as regards the fulcrum 23, the fulcrum position should be determined by a suitable procedure and taught to the manipulator controller. In case the fulcrum position is inaccurately defined, pivoting of the instrument 14 generates interaction forces with the abdominal wall that can mask the desired force/torque values at the instrument tip 20 and/or the fulcrum 23. These masking forces increase with the magnitude of the fulcrum position inaccuracy. In addition, such inaccuracy produces wear on the incision, which can lead to the release of the trocar 22, in turn provoking loss of abdominal pressure and thereby unnecessarily increasing the intervention time due to the required recovery of the situation.

The definition accuracy of the position of the fulcrum 23 depends not only on the procedure used to identify its position it but also on the static and dynamic accuracy of the robot manipulator 10. In the present application, a +/−2.5 mm estimate of overall fulcrum and manipulator accuracy could be acceptable considering the incision dimension and the elasticity of the abdominal wall. According to an experimental set-up, definition inaccuracies regarding the fulcrum 23 may lead to disturbances of 2N-10N at the level of the trocar 22.

As a result, an appropriate selection of the type of trocar 22 permits to avoid the gas tap disturbance and to reduce friction and weight disturbances along the axis of instrument shaft 18 to the level of typical human hand sensitiveness which is around 0.6N. Real-time monitoring of intra-abdominal pressure variations with respect to the pressure at initial fulcrum definition, can detect a variation of the true fulcrum location due to varying insufflation conditions. However, the disturbance force at the access port level (i.e. fulcrum 23 or pivot point), due to an inaccurate definition of the fulcrum 23 and due to motion inaccuracy of the manipulator 10, can be identified in real-time through the proposed method described hereinafter.

The proposed method and system are able to overcome the encountered disturbance issues, thereby enabling tele-operation with accurate force feed-back and a number of other beneficial safety-related functions based on force information, obtained exclusively from a sensor arrangement mounted onto the manipulator 10, i.e. outside the patient. There is no need for further sensors, neither on the instrument 14 nor on the trocar 22.

Calculating Forces at the Instrument Tip and at the Fulcrum Level

The proposed method permits to provide an accurate estimate of the forces $\overline{F_{Tip}}$ at the instrument tip 20 and $\overline{F_{Fulcrum}}$ at the fulcrum 23

An main point of this method is the calculation of the forces $\overline{F_{Tip}}$ and $\overline{F_{Fulcrum}}$, using the force and torque components measured by the F/TAS 30 which, as will be understood is located at a remote point with respect to the respective points of application of $\overline{F_{Tip}}$ and $\overline{F_{Fulcrum}}$. This calculation furthermore uses a determined position of the instrument 14 relative to the trocar 22, e.g. the distance between the fulcrum 23 and the origin of the SRF of the F/TAS 30 shown in FIG. 3. This calculation is based on several assumptions and pre-requisites, as follows:

A. The 6-DOF F/T sensor in the F/TAS 30 measures the three components of forces (Fx, Fy, Fz) and the 3 components of moments (Mx, My, Mz) produced by the load attached to the F/TAS 30 in a right-hand Cartesian frame as shown in FIG. 3 (SRF).

B. The instrument 14 is attached to the F/T sensor through a support, that can contain one or more actuators for the instrument mechanism as well as further other subsystems (i.e. the effector unit 12).

C. For purposes of ease of description, it is assumed that the effective reference frames of the 6-DOF F/T sensor and the the 6-DOF accelerometer of the F/TAS 30 coincide with the SRF shown in FIG. 3 in which the Z axis is collinear with the longitudinal axis of a mounted instrument 14 and points towards the instrument tip 20, the Y axis is parallel to the upper surface of the main body 24 and the origin is located on the sensing plate of the F/TAS 30. In case the forces and torques measured by the F/T sensor are expressed with respect to another frame, a transformation can be applied to express the measured forces and moment values with respect to the SRF.

D. The values of force and torque components used in the equations hereinafter are obtained from originally unfiltered 6-DOF F/T sensor measurements after subjecting the latter to compensation of electrical offsets, gravity and acceleration loads and a specific filtering process for reducing measurement noise as described hereinafter.

E. Only two external contact forces are applied to the instrument 14 as shown in FIG. 2, i.e. the reaction force at the fulcrum 23 ($\overline{F_{Fulcrum}}$), which is assumed to be tangent to the abdominal wall, and a contact force ($\overline{F_{Tip}}$) on the instrument tip 20 which may have any direction and sense.

F. The fulcrum reactio expressed in the SRF, noted $\overline{F_{Fulcrum}}$, has a null Z component and there are no external moments applied to the fulcrum 23.

G. The external force applied to the instrument tip 20 is expressed in the SRF and noted $\overline{F_{Tip}}$. $\overline{F_{Tip}}$ equals the opposite of the force exerted onto the tissue/organ contacting the instrument tip (actio+reactio=0). There are no external moments applied to the instrument tip 20.

H. The distance vector $\overline{D_{Fulcrum}}$ from the origin of the SRF to the fulcrum 23 is known and has a component along the Z axis only. In practice there may be X and Y components of a few millimeters if the shaft 18 of the instrument 14 is bent and therefore the distance along the Z axis may be slightly inaccurate. This distance vector $\overline{D_{Fulcrum}}$ can be determined, i.e. continuously updated from an initial reference, using procedures outlined hereinafter.

I. The distance vector $\overline{D_{Tip}}$ from the origin of the SRF to the instrument tip 20 is known and is aligned along the Z axis.

Taking into account the above assumptions, the resulting torque and moment in the SRF, respectively noted $\overline{T_s}$ and $\overline{F_s}$, can be calculated using the principle of superposition applied to forces and moments by means of the following equations:

$$\overline{T_s} = \overline{F_{Tip}} \times \overline{D_{Tool}} + \overline{F_{Fulcrum}} \overline{D_{Fulcrum}} \quad (10)$$

$$\overline{F_s} = \overline{F_{Tip}} + \overline{F_{Fulcrum}} \quad (11)$$

Where $\overline{D_{Tool}}$ represents the vector from the origin of the SRF to the instrument tip 20, which is collinear with the Z axis of the SRF.

Contact force components at the Instrument-tip 20 are determined by substituting $\overline{F_{Fulcrum}}$ in (10), which results in:

$$F_{Tip}(x) = \frac{T_S(y) - F_S(x) * D_{Fulcrum}(z)}{D_{Tip}(z) - D_{Fulcrum}(z)} \quad (12)$$

$$F_{Tip}(y) = \frac{T_S(x) + F_S(y) * D_{Fulcrum}(z)}{D_{Fulcrum}(z) - D_{Tip}(z)} \quad (13)$$

$$F_{Tip}(z) = F_S(z) \quad (14)$$

Similarly, force components at the fulcrum 23 are:

$$F_{Fulcrum}(x) = \frac{T_S(y) - F_S(x) * D_{Tip}(z)}{D_{Fulcrum}(z) - D_{Tip}(z)} \quad (15)$$

$$F_{Fulcrum}(y) = \frac{T_S(x) + F_S(y) * D_{Tip}(z)}{D_{Tip}(z) - D_{Fulcrum}(z)} \quad (16)$$

As will be appreciated, an accurate estimation of the contact forces $\overline{F_{Tip}}$ and $\overline{F_{Fulcrum}}$ applied at the instrument tip 20 and at the fulcrum 23 respectively, allows, among others, improvements in safety and quality of robotically assisted minimally invasive medical procedures. For instance, the assumed location of the fulcrum 23 with respect to which the robot manipulator 10 is moved, can be continuously adjusted by the robot control software, in real-time during the procedure, towards a point of minimum resistance using $\overline{F_{Fulcrum}}$. Furthermore, the contact forces at the instrument tip 20 can be reflected by the (master) arm with which the surgeon commands the (slave) robot manipulator 10, so as to enable tactile sensing.

Determining the Instrument Position Relative to the Fulcrum

An initial reference position of the instrument relative to the fulcrum, e.g. distance $\overline{D_{Fulcrum\ 0}}$ can be determined through the procedure set out below, when a given instrument 14 is inserted for the first time in the trocar 22. Using the initial reference distance $\overline{D_{Fulcrum\ 0}}$, $\overline{D_{Fulcrum}}$ is subsequently continuously updated (i.e. determined in real-time) using the commanded penetration/extraction, which is a function of the motion of the manipulator, which in turn is known from the manipulator controller.

An example of the procedure to determine the initial fulcrum position (reference distance $\overline{D_{Fulcrum\ 0}}$) is based on the assumption that the fulcrum 23 is the point of minor force resistance and can be found using the F/T sensor on the effector unit 12. For this procedure, it is assumed that the X and Y axes of the SFR lie in the front plane of the sensing plate of the F/T sensor while the Z component is collinear with the instrument shaft 18. The procedure is outlined as follows:

Step 1—Insertion of the instrument 14, that is attached to the manipulator 10, into the trocar 22, until the instrument tip 20 is seen on the endoscope monitor (i.e. exiting the trocar sleeve).

Step 2—Determination of the position of the instrument 14 that gives the lowest reaction forces along the X and Y axes of the SRF, by sliding the instrument 14 along these axes until reaction forces are below a given threshold, e.g. of 0.3N. Once a suitable point is found, it can be assumed that the fulcrum 23 is located at a certain point along the instrument axis, i.e. on the Z axis.

Step 3—Determination of the position of the fulcrum 23 (Z axis coordinate) on the instrument axis (which corresponds to the Z axis) using the lever principle, where the distance at which the force is applied is equal to the module of the moment vector divided by the module of the force vector.

Since at step 2, the instrument position corresponds to a near-zero contact force ($\overline{F_{Fulcrum}}$) the instrument 14 is pivoted with respect to its tip 20 until a sufficient contact force (about 3N) is reached. At this point the distance is computed according to the lever principle. Subsequently, the instrument is pivoted in the opposite direction until the same contact force value is measured and the again the distance is computed again. Thereafter, the instrument 14 is pivoted to its initial position determined in step 2. The reference distance $\overline{D_{Fulcrum\ 0}}$ between the fulcrum 23 and the origin of the SFR on sensor (along the Z axis) is set to the mean value of the last two measurements.

As both, the position and orientation of the SRF in the world reference frame and the initial reference distance $\overline{D_{Fulcrum\ 0}}$, giving the position of the fulcrum 23 with respect to the SRF (i.e. sensor) resting at the location found in step 2, the fulcrum location with respect to the world reference frame can be computed through a simple change of reference frame (transformation of coordinates).

Afterwards, all moves (pivot and penetration) can be given with respect to the fulcrum 23, and the instrument position relative to the fulcrum 23, e.g. the distance between the origin of the SRF and the fulcrum 23, can be updated accordingly e.g. using position information from the manipulator controller.

Compensation of Offsets and of Gravity and Dynamics Loads

As will be understood, the force/torque sensor, e.g. in the F/TAS 30, attached to the robot manipulator 10, measures not only the contact forces $\overline{F_{Tip}}$, $\overline{F_{Fulcrum}}$ but also the gravity load as well as dynamic (i.e. motion-related) loads exerted onto the components attached to the sensing plate of the sensor.

Therefore, the method of force estimation provides for compensations of these loads using additional measurements obtained from the 6-DOF accelerometer associated to the 6-DOF F/T sensor.

The compensated force vector $\overline{F_{comp}}$ with respect to the sensor reference frame (SRF) is given by:

$$\overline{F_{comp}} = \overline{F_{sensor}} - \overline{F_{offsets}} - \text{LoadMass} \cdot ((\overline{\text{LinAcc}_{sensor}} - \overline{\text{LinAcc}_{offsets}}) + ((\overline{\text{AngAcc}_{sensor}} - \overline{\text{AngAcc}_{offsets}}) \times \overline{\text{Load}_{COG}})) \quad (17)$$

where:
- $\overline{F_{sensor}}$ is the force vector in the SRF as measured by the F/T sensor;
- $\overline{\text{LinAcc}_{sensor}}$ is the linear acceleration, including the gravity acceleration, measured by the 6-DOF accelerometer in the SRF;
- $\overline{\text{AngAcc}_{sensor}}$ is the angular acceleration measured by the 6-DOF accelerometer in the SRF;
- $\overline{\text{Load}_{COG}}$ is the vector of the center of gravity of the load attached to the 6-DOF F/T sensor in the SRF, that is estimated as outlined hereinafter;
- $\overline{F_{offsets}}$, $\overline{\text{LinAcc}_{offsets}}$ and $\overline{\text{AngAcc}_{offsets}}$ are vectors of sensor offsets, that are estimated during a calibration procedure outlined hereinafter;

The compensated torque vector $\overline{T_{comp}}$ with respect to the sensor reference frame (SRF) is given by:

$$\overline{T_{comp}} = \overline{T_{sensor}} - T_{Offset} - ((\overline{\text{Load}_{COG}} \times \overline{F_T}) + \text{LoadInertia} \cdot (\overline{\text{AngAcc}_{sensor}} - \overline{\text{AngAcc}_{offsets}})) \quad (18)$$

where:
- $\overline{T_{sensor}}$ is the moment vector in the SRF as measured by the F/T sensor;
- $T_{Offset}$ is the moment offset vector, estimated as outlined hereinafter;
- $\overline{F_T}$ equals the third term on the right-hand side of (17) which represents the force produced by the effect of gravity and of acceleration-related loads, which exerts a torque onto the sensing plate of the F/TAS 30;
- LoadInertia is the vector of the load inertia about SRF axes X, Y and Z, that can e.g. be estimated by visual tuning in an off-line analysis, i.e. observing the compensation accuracy improvement on a measurement plot for different values of the inertia vector.

As regards the effect of Coriolis acceleration, which depends on the angular acceleration and linear velocity of a moving frame with respect to a fixed one, it may be noted that this effect does not need to be taken into account with the present system, because forces and torques are measured with respect to the moving reference frame of the F/T sensor (SRF).

The effect of the centrifugal acceleration along the instrument stem axis, i.e. the Z-axis of the SRF, in the presented system has empirically been found to be less than 0.2N for typical instrument moves and less that 0.4N for fast moves in minimally invasive procedures. Although mentioned for the sake of completeness, it has been experimentally found that this effect can be neglected and is therefore not taken into account in equations (17) and (18).

For a typical system setup, experimental results in no-contact but fast moves, i.e. about 60 degrees/second for pitch and yaw pivot DOF and 150 mm/sec for the penetration/direction, show that forces are compensated within a +/−0.25N window, and that moments are compensated within a +/−0.03 Nm window approximately.

As will be understood, the compensated force and torque vector will be used for the calculation described in section "Calculating forces at the instrument tip and at the fulcrum level", i.e. $\overline{F_{comp}} = \overline{F_s}$ and $\overline{T_{comp}} = \overline{T_s}$.

Calibration Procedure

In order to determine system related parameters that affect measurement accuracy and calculations for force estimation, a suitable fitting technique, e.g. a least-squares fitting method, is applied on a series of measured data. In order to obtain data series for applying the least-square fitting technique, the robot manipulator 10 is consecutively positioned through a suitably predefined set of measurement poses distributed over the workspace of the robot manipulator 10. At each pose, corresponding to a different position and orientation of the F/TAS 30 through different configurations of the 6 DOF of the manipulator 10, the robot manipulator 10 is at rest when measurement data is read from the sensors of the F/TAS 30. The set of poses is preferably chosen so as to cover a sufficient range ("orientation workspace") of the following orientation angles: rotation about the Z-axis of the SRF ("roll") and either rotation about the pitch or the yaw pivot axis (for instance using a wrist articulation/joint that varies the sensor orientation with respect to gravity).

If appropriately chosen, it is safe to assume that the F/TAS 30 is factory-calibrated and that the accuracy and the resolution of the sensor are far beyond the application requirements. In this case, the fitting technique applied to the measurement data series enables among others accurate identification of (electrical) offsets of force and torque component measurements on each axis as well as (electrical) offsets of linear acceleration component measurement on each axis. Furthermore, the mass LoadMass and centre of gravity (COG) of the load attached to the sensing plate of the F/TAS 30 can be accurately determined using the calibration procedure as described below.

For the determination of force measurement offsets ($\overline{F_{offsets}}$), the effective load mass (LoadMass), and the linear acceleration offsets ($\overline{\text{LinAcc}_{offset}}$), the following equation is used:

$$\overline{F_{sensor}} = \overline{F_{offsets}} + \text{LoadMass} * (\overline{\text{LinAcc}_{sensor}} - \overline{\text{LinAcc}_{offset}}) \quad (21)$$

where:
- $\overline{F_{sensor}}$ is the force vector, as measured by the F/T sensor, in the SRF;
- $(\overline{\text{LinAcc}_{sensor}} - \overline{\text{LinAcc}_{offset}})$ gives the orientation of the gravity force with respect the SRF, since the linear acceleration measurement ($\overline{\text{LinAcc}_{sensor}}$) comprises the gravity acceleration term in addition to the motion-related acceleration (=null at rest) and an electrical offset ($\overline{\text{LinAcc}_{offset}}$)
- LoadMass*$(\overline{\text{LinAcc}_{sensor}} - \overline{\text{LinAcc}_{offset}})$ is the weight force vector given by the mass of the payload attached to the F/TAS 30 and by its orientation, with respect to the SRF For the determination of moment measurement offsets ($\overline{T_{offsets}}$) and of the coordinates of the centre of gravity of the payload with respect to the SRF ($\overline{\text{Load}_{COG}}$), the following equation is used:

$$\overline{T_{sensor}} = \overline{\text{Load}_{COG}} \times \text{LoadMass} * (\overline{\text{LinAcc}_{sensor}} - \overline{\text{LinAcc}_{offset}}) + \overline{T_{offsets}} \quad (22)$$

where (LoadMass, $\overline{\text{LinAcc}_{offset}}$) are as indicated above, see (21). For the determination of the linear acceleration measurement offsets, the equation is:

$$\text{MODULUS}(\overline{\text{LinAcc}_{sensor}} - \overline{\text{LinAcc}_{offset}}) = 1G \quad (23)$$

where:
- G is the gravity constant.

As will be understood, vector equations (21), (22) and (23) provide 7 scalar equations with 13 unknowns for every measurement of the F/TAS sensor in a given calibration pose of the manipulator 10.

Since the robot manipulator 10 and hence the F/TAS 30 is at rest in each pose, i.e. there is no motion when the measurements are taken, the offsets of the angular acceleration components can be estimated based on a mean value of angular acceleration measurements for all poses:

$$\text{MEAN}(\overline{\text{AngAcc}_{sensor}}) = \overline{\text{AngAcc}_{offset}} \quad (24)$$

Where:
$\overline{\text{AngAcc}_{sensor}}$ is the angular acceleration vector measured by the accelerometer;
$\overline{\text{AngAcc}_{offset}}$ is the electrical offset vector for the angular acceleration component The pose set shall be selected to cover the orientation workspace of the manipulator 10 in the surgical application. For instance, such an orientation workspace shall sample the roll angle about the Z axis of the SRF and the orientation angle given by the Z axis of the SRF with respect to the gravity axis. Experimentally, a number of 30 poses, corresponding to 210 equations, has generally been found sufficient for a satisfactory approximation of the required system parameters.

Since electrical offsets can differ at every start-up, the calibration procedure should be executed at start-up before using any measurements from the F/TAS 30. As described in section "Check of offset drifts", it may be advantageous to repeat the calibration procedure also during an intervention in order to take into account offset drifts. In this case, the system needs to drive the manipulator 10 through the set of poses, which has to be done in safe conditions.

An interesting aspect of this calibration method is that there is no need for knowledge of the position and orientation of the end-effector (e.g. effector unit 12), which also means that this method is independent of the robot manipulator accuracy. Therefore, for applications where compensated forces have to be measured, e.g. on hand-held portable devices, a simple manually actuated, i.e. passive, positioning device can be subjected to the present calibration procedure.

As will be understood, the above calibration procedure with subsequent approximation (data fitting method) allows among others to determine $\overline{F_{offsets}}$, $\overline{T_{offsets}}$, $\overline{\text{LinAcc}_{offsets}}$ and $\overline{\text{AngAcc}_{offsets}}$ used in equations (17) and (18) for compensation of offsets in the sensor data obtained from the F/TAS 30.

Sensor Data Filtering

A filtering technique should be applied to the raw measurement data obtained by means of the F/TAS 30. Although in principle many suitable techniques exist, the application of the basic classical form and of two variants of the discrete Kalman filter for linear stochastic processes is proposed in order to efficiently estimate acceleration and force/torque process variables, and in particular to reduce measurement noise inherent to the F/T sensor and accelerometer.

In a minimally invasive medical application using robotic tele-operation with force-feedback, apart from removing the signal noise to a satisfactory extent, it is highly desirable that the used filtering process complies with two additional requirements: firstly, the amplitude gain of filtered signals should be close to 1 (in the system bandwidth) in order to ensure force feedback fidelity and, secondly, the additional time delay that is introduced by the filter should be as short as possible. Preferably, the total tele-operation cycle delay, including the signal filtering delay should be less than 100 milliseconds in order that the surgeon does not visually notice a delay, e.g. in case of an instrument to tissue contact. Moreover, in order to avoid instability, e.g. when touching hard surfaces such as bones with the instrument tip 20, the total tele-operation cycle delay shall preferably be less than 20 milliseconds.

It has been experimentally found that a basic (digital) linear Kalman filter is a simple and efficient solution. Among others, it provides better noise rejection and dynamic behavior than some other filter types, in particular when compared to classical Tchebyscheff digital filters commonly implemented in the firmware of commercial force/torque sensors. As opposed to an extended Kalman filter type for the force and torque data processing, the present approach is applicable in real-time, is more easily tuned and avoids the need for knowledge of the non-linear dynamic model of the robot manipulator 10 which is difficult to identify precisely.

Since the aim of the filter is to estimate noisy digital signals which are measured separately and are not inter-correlated, an instance of the filter is applied individually to each of the following signal components:
Fx, Fy, and Fz for force measurements;
Mx, My and Mz for moment measurements;
Ax, Ay and Az for linear accelerations measurements;
Rx, Ry and Rz for angular accelerations measurements.

According to the basic Kalman filter, every signal can be assumed to be a process governed by a linear difference equation:

$$x_k = A x_{k-1} + B u_{k-1} + W_{k-1}$$

with a measurement $z \in \mathfrak{R}^1$ that is:

$$z_k = H x_k + v_k$$

In the present system we can assume for all signals that H=1 because the measurement is taken of the state directly and u=0, since there is no control input. Furthermore we assume for all signals: A=1 because the state is approximated to be invariant from step to step. However, in the case of forces and moments, the state varies according to gravity and acceleration loads, and for all other signals, the state is function of the operator motion commands, i.e. the behavior of manipulator 10. Therefore, this latter approximation assimilates the sources of state variations to process noise.

As will be appreciated, the proposed filter formulation is that of the basic discrete Kalman filter implementation which applies to linear stochastic processes. The related time update and measurement update equations of this filter implementation can be found e.g. in "An introduction to the Kalman Filter"; Greg Welch, Gary Bishop; UNC-Chapel Hill; 2002, as follows:

$$K_k = P_k^- H^T (H P_k^- H^T + R)^{-1}$$

$$\hat{x}_k^- = A \hat{x}_{k-1} + B u_{k-1} \qquad \hat{x}_k = \hat{x}_k^- + K_k (z_k - H \hat{x}_k^-)$$

$$P_k^- = A P_{k-1} A^T + Q \qquad P_k = (I - K_k H) P_k^-$$

time update equations    measurement update equations

As regards initialization, the following initialization parameters can be used for all signals:
covariance of the measurement noise R=1.0: although the best value is the real measurement noise covariance that could be obtained in a sensor calibration phase, any strictly positive value (R>0), meaning that the measurement is not trusted, can be used. In fact, the system/process noise covariance parameter Q determined during the filter tuning phase compensates for errors in the initial measurement noise covariance value R;

initial state value $x_{k-1}$=first observation;

initial Kalman gain value $K_k$=1.0;

initial system process/system noise covariance $Q_0$ determined by filter tuning.

It has been shown that the Kalman gain $K_k$ converges to the same constant value independently from the given parameters process/system noise covariance Q and measurement noise covariance R, usually after 50 cycles of the recursive iteration. With the present system, it has been found experimentally that after 150 msec (50 cycles), the Kalman gain $K_k$ converges towards the constant value, it remains constant after 4.5 sec (1500 cycles) and reaches the 99% window of its constant value after 2.1 sec (700 cycles). It has further been found that the Kalman gain $K_k$ remains constant irrespective of the (amplitude) of dynamic and contact loads affecting force and torque measurements, which validates the approach of a basic linear filter formulation.

As regards filter (parameter) tuning, an approach based on comparing the unfiltered signal with the filtered signal on the same real-time plot for different values of system/process noise covariance Q and in real tele-operation conditions (e.g. at 1:1 motion scale, with accelerated moves of the manipulator 10 but without contact forces exerted onto the instrument 14) can be used.

The general purpose of tuning is to obtain a filtered signal without spikes or high frequency ripple, that averages the unfiltered signal but with little response delay on signal transitions (time-lag). In the present context, response delay means the filter inherent time-lag between the filtered signal and the "true" unfiltered signal observed during signal variations. For force, torque and acceleration signals which are used in the compensation process (see chapter "Compensation of offsets and of gravity and dynamics loads in sensor data"), all signals should be filtered with the same covariance parameters R, Q in order to maintain an identical time-delay behavior for each signal, especially as regards signal transitions. Experimentally, this approach proves to be consistent and can be justified by the fact that the same physical phenomenon, i.e. motion acceleration of the manipulator 10, nearly exclusively determines the dynamic behavior of the measured signals.

As regards a qualitative analysis, it has been demonstrated that, for static signals affected by noise, the Kalman filter is as optimal estimator with 1:1 gain. For dynamic signals, as in the present system, the Kalman filtered signal does not have spikes due to noise because the noise is almost entirely removed, and the filtered signal has similarity to an averaged signal with transitions smoothness depending on the chosen process noise covariance parameter Q.

It will be understood that, with a smaller process noise covariance Q, the filtered signal becomes smoother because the measurement is less trusted, and vice versa. Furthermore, with lower values of the process/system noise covariance Q set in the Kalman filter, not only the smoothness of the filtered signal but also the response delay caused by the filtering process increases for a given measurement noise covariance R. It is however desirable to have both an immediate and a smoothly varying force estimate, e.g. for feed-back to the master arm of a tele-operation command console. Table 1 shows typical response delays for different process noise covariance parameters Q of a force signal (e.g. on the X-axis of the SRF).

TABLE 1

X-axis Force signal filtered with Kalman during tele-operation

| Process covariance parameter Q | Response delay in intervals | Response delay in ms |
|---|---|---|
| 1 | 0.4 | 1.172 |
| 0.1 | 3 | 8.79 |
| 0.01 | 11 | 32.23 |
| 0.001 | 25 | 73.25 |
| 0.0001 | 40 | 117.2 |

The response delays indicated in Table 1 were evaluated off-line, with measurement noise covariance R=1.0, by measuring the time-lag between the filtered signal obtained with the basic linear Kalman filter and the signal obtained using a parallel backward recursion (RTS) form of the Kalman algorithm, as described in "Maximum likelihood estimates of linear dynamic systems"; H. Rauch, F. Tung, and C. Striebel; American Institute of Aeronautics and Astronautics Journal; 3 (8), 1965, which optimally follows the original "true" signal without introducing response-delay.

Figure 4:
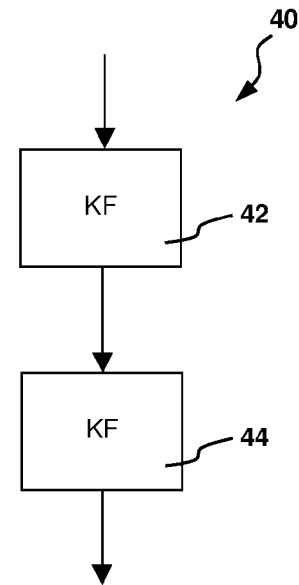
FIG. 4 is a block schematic diagram of a cascaded linear Kalman filter.

In order to reduce the filter inherent response delay, the cascaded filter implementation 40 as shown in FIG. 4 is proposed. This filter cascade 40 comprises a first filter stage 42 and a second filter stage 44, each filter stage 42, 44 being a separate implementation of a basic linear Kalman filter as described above. The first filter stage 42 is configured to lower the covariance i.e. to reduce the peaks (noise spikes) of the noise affecting the unfiltered signal but to cause only a relatively short response delay (e.g. 2-3 ms). The second filter stage 44, is configured to provide a substantially smooth output signal and therefore introduces a longer response delay (e.g. 15 ms) than the first filter stage 42.

It has been found that, for a given total response delay, two cascaded filters improve the smoothness of the filtered signal with respect to a single filter causing the same response delay. In order to achieve this, e.g. in a two filter cascade as shown in FIG. 4, the first filter stage 42 is configured with a system/process error covariance ($Q_1$) that is significantly greater than the system/process error covariance of the second filter stage 44 ($Q_2$) with given identical measurement error covariance R. Thereby, the same filtering performance at lower total response delay when compared to a single stage Kalman filter can be achieved. In other words, a Kalman filter cascade with a given total response delay provides better filtering performance than a single stage Kalman filter with the same response delay. By experiment, it has been found e.g. that two cascaded Kalman filters, the first and second filter stages 42, 44 being configured with identical measurement noise covariance R=1 and different system/process error covariance parameters of $Q_1$=0.7 and $Q_2$=0.012 respectively, improve the smoothness of the final filtered signal with respect to a single stage filter configured with Q=0.01 and producing the same observed response delay (=32 ms). Preferred parameter ranges for the noise covariance Q1 and Q2 of the first and second filter stage 42, 44 respectively are: $0.1 \leq Q_1 \leq 1$ and $0.001 \leq Q_2 \leq 0.1$. Preferably, the total response delay should not exceed 40 ms for reducing the risk of instability on hard surfaces contact.

Therefore, a cascade of at least two linear Kalman filters is preferred since it introduces less response delay with respect to a single-pass (one stage) filter giving the same filtering performance (signal smoothness). It should be noted that the respective filter implementation for each unfiltered signal ((Fx, Fy, Fz); (Mx, My, Mz); (Ax, Ay, Az); (Rx, Ry, Rz)) will usually be configured with the same filter parameters ($Q_i$, $R_i$, etc.) in order ensure an identical response delay on all signals and, thereby, synchronized signals.

Check of Offset Drifts

As will be understood, every component measurement (signal) obtained from the of F/T sensor and accelerometer in the F/TAS 30 is affected by an electrical bias or offset that is normally time-varying and temperature dependent. In laboratory trials it has been found that measurement signals from a 6-DOF foil-based F/T sensor (with built-in temperature compensation) stabilize after a warm-up period of about 3 hours, and remain thereafter within a range of about 1.5% of the full measurement scale. However, the offset value for each signal is subject to variation over time and, in case of a medical, especially a surgical application, this variation may be unacceptable, as it alters the calculation results for estimating the forces as described hereinbefore.

Therefore, it is proposed to include a procedure for checking that these offsets remain within an acceptable range. This can be achieved in simple manner by checking whether the compensated force and torque vector $\overline{F_{comp}}$. $\overline{T_{comp}}$ components are near zero when no external loads are applied on the payload attached to the F/TAS 30.

The proposed function can consist in a software implemented procedure carrying out the check upon command request. In case of excessive offset drift, the procedure sends a warning to the manipulator controller, which should for example ask the surgeon to initiate a re-calibration process. Furthermore, this function can be carried during a surgical instrument change, either upon a command given on the HMI or automatically, for example based on the signal of a surgical instrument presence-detector on the effector unit 12.

Software Module Architecture

Initially, it may be noted that the software architecture described hereinafter is refers to a software module whose purpose is limited to data processing and calculations for estimation of contact forces at the level of the instrument tip 20 and at the level of the fulcrum 23. It does not take into account functions and mechanisms to the control of the manipulator 10, the effector unit 12 or other components of the system. This module can however be integrated in the software program of a manipulator controller by the skilled person.

Figure 5:
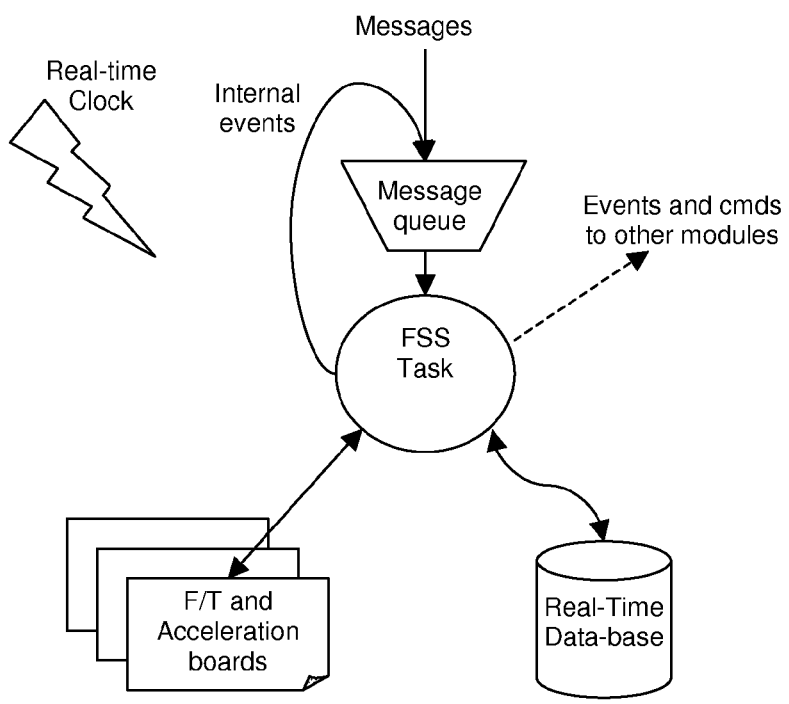
FIG. 5 is a block schematic diagram of a software architecture for performing the method according to the invention.

The general architecture of the software module is schematically shown in FIG. 5. It comprises a core process, the FSS (force sensing system) task which is governed by a state transition diagram described hereinafter, that can be implemented in a main function running either in task context or at interrupt service routine level. For the sake of simplicity, it is assumed that the software module runs in a periodic task synchronized by a real-time clock through a semaphore as shown in FIG. 5. The FSS task is run at a given priority in the real-time operating system and with a given stack size. The software module has a message queue that is polled at each clock cycle for new messages. There are generally two types of messages: command messages to execute a function or event messages to generate a transition in the state transition diagram (see below). Command messages are generated by external modules pertaining to e.g. the manipulator controller, whereas event messages are issued internally by the software module itself. The module is capable of generating event and command messages directed to other, e.g. manipulator controller modules, for example in order to issue failure events, command replies or stop_motion commands.

In the software module, the main interfaces of the FSS task are, as shown in FIG. 5:
- a message queue, read at every clock cycle;
- an interface to hardware boards from which unfiltered force, torque and acceleration data is read;
- an interface to a real-time data base to read information required by the functions of the modules and to write results
- an interface for commands and event messages to external modules.

State Transition Diagram (FSS Task)

FIG. 6 shows the main five states of the Force Sensing System (FSS) task (cf. FIG. 5) implemented as finite state machine. In the following, the states shown in FIG. 5 will be briefly described:

State 1: Hardware and software initialization: this state concerns the initialization procedures for the software and hardware parts of the minimally invasive medical system. These initialization procedures are carried out at power-up and/or at boot time of the controller of the manipulator 10. The hardware initialization task concerns among others the set-up of the F/T sensor and accelerometer, e.g. of the F/TAS 30, and the related interface board(s). The software initialization task includes the steps of allocating resources such as memory for data structures of the application, and other operating-system items (i.e. tasks, semaphores, message queues, clocks, etc.). If the hardware and software initialization succeed, the system enters an IDLE state, waiting for the calibration command. Otherwise, the system enters a FAILED state as shown in FIG. 6. The result of the initialization operation can be communicated to the controller of the manipulator 10, either through a software event or through a function call returned parameter.

State 2: IDLE state: the system waits for a command to start the calibration process, which has been described in section "Calibration procedure".

State 3: FAULT state: this state is entered in case of any system/software malfunction or in case of a detected safety risk, the system waits for a restart command. Upon entering the FAULT state, an asynchronous message or event is sent to the manipulator controller in order to warn of this condition.

State 4: F/T_&_ACCELEROMETER_CALIBRATION state: In this state, the manipulator 10 is commanded through a predetermined set of poses with different positions and orientations (see section "Calibration procedure"). In each pose, the F/T sensor and accelerometer data are recorded upon the reception of a 'record' command. After the completion of the pose set, upon the reception of a 'compute' command, the aforementioned least-squares fitting technique, or any other suitable approximation technique, is applied in order to calculate F/T sensor and accelerometer offsets ($\overline{F_{offsets}}$, $\overline{T_{offsets}}$, $\overline{LinAcc_{offsets}}$ and $\overline{AngAcc_{offsets}}$) together with the coordinates of the centre of gravity of the attached load. In the unlikely event the calculation fails, e.g. because of inconsistent results or because of a user-made abort command of pose set moves, the system returns into the IDLE state warning the manipulator controller of this event.

Otherwise, at the end of the calibration phase, the system passes into the APPLICATION_LOADS_EVALUATION state. In case of software or hardware failure detection, the system passes to the FAULT state.

State 5: APPLICATION_LOADS_EVALUATION state: In this state, a periodic process executes sequentially, but not necessarily in the given order, the following operations:

Data filtering, e.g. by means of a discrete Kalman filter cascade for linear stochastic processes (see section "Sensor data filtering");

Compensation of the effect of gravity and dynamic loads in F/T sensor data (see section "Compensation of offsets and of gravity and dynamics loads");

Determination, i.e. continuous updating based on manipulator 10 motion, of the position of the instrument 14 relative to the fulcrum 23 (see section "Determining the instrument position relative to the fulcrum")

Calculate an estimate of the forces at the instrument tip 20 and at the fulcrum respectively (see section "Calculating forces at the instrument tip and at the fulcrum level");

Optionally the following further operations are also executed by the periodic process:

Monitoring of compensated loads against predetermined maximum threshold values e.g. stored in the real-time data-base. In case of exceeding values, the function issues a warning message, or a stop motion command and writes this condition in the real-time database; this process can also be applied to the estimated forces at the instrument tip 20 and at the fulcrum level (trocar 22) in order to detect unsafe conditions or a failure of the F/TAS 30;

Check the drift of sensor offsets (see section "Check of offset drifts");

Monitoring the intra-abdominal insufflation pressure. In case of depressurization, the function issues a warning message so that appropriate action ca be taken, among which e.g. redefining the position of the fulcrum 23.

FIG. 7 shows a possible sequence of the above operations in a flow chart. As seen in FIG. 7, a primary linear Kalman filter, of cascaded configuration e.g. as described with respect to FIG. 4, filters the sensor data prior to compensation of the "parasitic loads". After compensation, a secondary linear Kalman filter is applied to the force and torque values, in order to further improve the smoothness quality of the signal at the input of the operation that calculates the force estimate(s) (Compute $\overline{F_{Tip}}$ and $\overline{F_{Fulcrum}}$). Although shown in FIG. 7 as executed before the step of calculating the force estimates, the operation for determination of the instrument position can be executed periodically at another point in the flow. Similarly one or more of the above optional operations (indicated by block " . . . " in FIGS. 7 and 8) need not necessarily be executed subsequent to calculating the force estimates.

FIG. 8 shows an alternative sequence of the above operations in a flow chart. As seen in FIG. 8, a single filtering operation is applied subsequent to calculating the force estimate(s) (Compute $\overline{F_{Tip}}$ and $\overline{F_{Fulcrum}}$). The filtering operation can be based on a cascaded Kalman filter configuration as described with respect to FIG. 4.

The alternative of FIG. 8 reduces the loss of information (under-/overrated loads) due to filtering, prior to calculation of the force estimate(s), such that a further increase in accuracy can be achieved. The embodiment of FIG. 7 is preferable in case the system is configured for using the effector unit 12 as a control device ("joystick") for assisted positioning of the manipulator 10 e.g. during insertion of the instrument 14.

In case, a request for recalibration is received, the state of the system is changed to F/T_&_ACCELEROMETER_CALIBRATION and the periodic process is stopped. In case of a software or hardware failure detection, the system is changed to the FAULT state and a warning is issued.

The execution rate of the cyclic process is configured according to the applications requirements. For instance, when using the compensated data for robotic tele-operation, this process shall preferably be run at the same rate as that of the set-point generation for the manipulator 10, e.g. between 300 Hz and 1000 Hz.

CONCLUSION

The presented method/system provide a contribution to robotic and/or computer assisted minimally invasive surgery by offering an accurate and cost-effective way of estimating the contact forces at the instrument tip and, optionally, at the trocar level.

In laboratory trials of a prototype system, an average estimation error of 0.25N and a maximum estimation error of 0.65N have been determined. It will be appreciated, that even though these values were achieved using a prototype under development, the estimation error level is satisfactory even for most tasks in surgical laparoscopy, since 0.25N is below the sensitivity threshold of the human hand. Furthermore, it will be appreciated the a total signal delay of 50 ms achieved with the prototype make the system readily suitable for tele-operation.

The invention claimed is:

1. A minimally invasive medical system, comprising:
a manipulator;
a detachable minimally invasive instrument having a first end and a second end; an effector unit connected to the manipulator, the effector unit configured to hold the first end of the detachable minimally invasive instrument;
a trocar configured to be mounted on a patient, wherein the second end of the instrument is configured to be positioned inside the patient through the trocar and beyond a fulcrum, the trocar configured to define said fulcrum which kinematically constraints the instrument;
a six-degrees-of-freedom force-torque sensor disposed between said effector unit and said manipulator and between said first end of the instrument and said manipulator, said sensor configured to measure forces and torques exerted onto said effector unit by said first end of the instrument;
a programmable computing device configured to:
  determine an initial reference position of the detachable minimally invasive instrument relative to said fulcrum and to continuously update the position using manipulator motion information;
  determine the position of said instrument relative to said fulcrum based on said determined initial reference position and on said continuously updated position;
  and apply the principle of superposition to calculate an estimate of a force exerted onto the second end of said instrument based on said determined position, said measured force and said measured torque, wherein the measured force and measured torque used to calculate said estimate being only force and torque measured using the six-degrees-of-freedom force-torque sensor; and
  provide haptic feedback signals to the manipulator based on said estimate.

2. The system as claimed in claim 1, wherein the programmable computing device is further configured to apply the principle of superposition to calculate an estimate of a force exerted at said fulcrum by said instrument, based on said determined position, said measured force and said measured torque.

3. The system as claimed in claim 1, wherein said effector unit is equipped with a six-degrees-of-freedom accelerometer configured to measure a gravity load or dynamic loads exerted onto said six-degrees-of-freedom force-torque sensor, and wherein the programmable computing device is further configured to process measurements made with said six-degrees-of-freedom accelerometer and to compensate said gravity or dynamic loads in said measured force and said measured torque.

4. The system as claimed in claim 1, wherein said programmable computing device is further programmed to apply a linear Kalman filter to force and torque data measured with said six-degrees-of-freedom force/torque sensor prior to calculating said estimated force.

5. The system as claimed in claim 1, wherein said programmable computing device is further programmed to apply a linear Kalman filter to said calculated force estimate.

6. The system as claimed in claim 3, wherein said programmable computing device is further programmed to apply a primary linear Kalman filter to force and torque data measured with said six-degrees-of-freedom force-torque sensor and to linear and angular acceleration data measured with said six-degrees-of-freedom accelerometer; compensate disturbances due to gravity and dynamic loads after application of said primary linear Kalman filter; and apply a secondary linear Kalman filter to said compensated force and torque data.

7. The system of force estimation as claimed in claim 6, wherein said linear Kalman filter is cascaded and has a first linear Kalman filter stage with a process noise covariance parameter set to a higher value in the range between 0.1 and 1, and a second linear Kalman filter stage with a process noise covariance parameter set to a lower value in the range between 0.001 and 0.1.

8. The system of force estimation as claimed in claim 7, wherein at least one of said primary linear Kalman filter and said secondary linear Kalman filter is cascaded and has a first linear Kalman filter stage with a process noise covariance parameter set to a higher value in the range between 0.1 and 1, and a second linear Kalman filter stage with a process noise covariance parameter set to a lower value in the range between 0.001 and 0.1.

* * * * *